(12) United States Patent
Simon et al.

(10) Patent No.: US 7,179,495 B1
(45) Date of Patent: Feb. 20, 2007

(54) HYPERFORIN AS CYTOSTATIC AGENT AND HYPERFORIN OINTMENT OR CREAM AS APPLICATION FORM

(75) Inventors: Jan C. Simon, Merzhausen (DE); Christoph M. Schempp, Freiburg (DE); Erwin Schoepf, Freiburg (DE); Birgit Simon-Haarhaus, Gundelfingen (DE)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

(21) Appl. No.: 09/856,694

(22) PCT Filed: Nov. 24, 1999

(86) PCT No.: PCT/EP99/09067

§ 371 (c)(1),
(2), (4) Date: Aug. 13, 2001

(87) PCT Pub. No.: WO00/30660

PCT Pub. Date: Jun. 2, 2000

(30) Foreign Application Priority Data

Nov. 25, 1998 (DE) ................................ 198 54 446
Mar. 24, 1999 (DE) ................................ 199 13 333

(51) Int. Cl.
*A61K 36/00* (2006.01)
*A61K 36/38* (2006.01)

(52) U.S. Cl. ....................................... 424/730; 424/725

(58) Field of Classification Search ................ 424/725, 424/730
See application file for complete search history.

(56) References Cited

U.S. PATENT DOCUMENTS 4,021,553 A * 5/1977 Lacefield et al.
4,911,925 A   3/1990 Shatkina et al.
5,151,534 A * 9/1992 Shroot et al.

FOREIGN PATENT DOCUMENTS

EP      0 424 534 A1   5/1991
GB      2311009        9/1997
WO      WO 91/15218    10/1991
WO      WO 91/15218 A1 10/1991
WO      WO 95/11035    4/1995
WO      WO 97/39355    10/1997

OTHER PUBLICATIONS

The Hypericum Home Page, http://www.hypericum.com/hyp20.htm, 1996.*

DeCosterd et al., "New Hyperforin Derivatives from Hypericum-revolutum Vahl with growth-inhibitory activity against a huma colon carcinoma cell line", HELV CHIM ACTA, 1989, 72 (3), 464-471.* http://www.merck.com/pubs/mmanual/section10/chapter111/111a.htm, printed Apr. 29, 2002.*

Valavicius et al., "Antitumor activity of herbs of the Lithuanian SSR", Lietuvos TSR Mokslu Akademijos Darbai Serja Biologijos Mokslai, 1986, Series B, pp. 110-113 (translated).*

Mikrobiologicheskii Zhurnal, Higher Plants As A Source For Production Of New Antibiotics, Database Biosis (Online), 1978, Biosciences Information Service Philadelphia, PA U.S. Abstract Only.

Valavichyus Yu M; Ivanauskas V P; Yaskonis Yu A, Antitumor Activity Of Medicinal Plants From The Lithuanian SSR USSR 6. Common St. John's-Wort and Chamomilla-Recutita, Database Biosis (Online), 1986, Bioseiences Information Service, Philadelphia, PA U.S. Abstract Only.

J.E.F. Reynolds, Martindale, The Extra Pharmacopoeia, Thirtieth Edition, 1993, Pharmaceutical Press, London GB, 1993, p. 1378, 1902.

Inomata, Shinji et al., Antiaging agents containing extracts of Hypericaceae plant and Antiaging Cosmetics, Chemical Abstracts, Dec. 20, 1999, vol. 131, No. 25, Zusammenfassung & Patents Abstracts of Japan, Columbus, Ohio U.S.

Pishkina Ki, Herbal Composition For Treating Mastitis In Lactating Animal's—Including Extracts Of Calendula, Nettle, Plantain, Origanum, St. John's Wort, Thyme, Linden and Celandine, Emulsifier and Vegetable Oil, Dec. 20, 1996, Database WPI, Derwent Publications, Ltd., London, GB Abstract Only.

La Decosterd, H. Stoeckli-Evans, J.C. Chapuis, J.D. Msonthi,. Sordat, K. Hostettmann, New Hyperforin Derivatives From Hypericum-Revolutum Vahl With Growth-Inhibitory Activity Against a Human Colon Carcinoma Cell Line, 1989, Bd. 72, Nr 3.

M.L. Chavez, P.L. Chavez, Monographs On Alternative Therapies: Saint John's Wort, Hospital Pharmacy, 1997, p. 1621-1628, 1631-1632, vol. 32.

E. Steoabivam A. Saraf, G. Sukolin, Treatment of Atopic Dermatitis With Original Natural Creas, 1996, p. 167, Allergy, Copenhagen.

P. Maisenbacher et al., "Analysis and Stability of Hyperici Oleum", Planta Med., Aug. 1992, pp. 351-354 vol. 58, No. 4, abstract only.

* cited by examiner

*Primary Examiner*—Ruth A Davis
(74) *Attorney, Agent, or Firm*—Heller Ehrman LLP

(57) ABSTRACT

The invention relates to the use of hyperforin for treating cancer diseases and/or precancerous stages. In addition, the invention relates to a hyperforin-containing ointment or cream and to its production and use. The hyperforin-containing ointment or cream is also suitable for treating inflammatory skin diseases, geriatric skin and bacterial skin diseases and also skin diseases in the sphere of veterinary medicine.

22 Claims, 9 Drawing Sheets

HYPERFORIN AS CYTOSTATIC AGENT AND HYPERFORIN OINTMENT OR CREAM AS APPLICATION FORM

The present invention relates to the use of hyperforin as a cytostatic agent and to a hyperforin ointment or cream which is suitable as a form for applying the hyperforin.

Hyperforin and the hypericins are characteristic constituents of St. John's wort (Hypericum perforatum L.), which also contains constituents which occur generally in the plant kingdom, such as flavone derivatives, flavonol derivatives, rutin, hyperoside, xanthone derivatives, amentoflavone, biapigenin and ethereal oils.

St. John's wort and St. John's wort extracts have already been employed for some considerable time in medicine and folk medicine as drugs for a wide variety of indications. The constituent hypericin has also recently come to be used in drugs as an active compound in isolated form (L. Roth, Hypericum, Hypericin, Ecomed medicinal plant monograph. Ecomed, Landsberg/Lech, 1990).

The monograph "Hyperici herba (St. John's wort)", which as published by commission E of the former Public Health Office on 5.12.1984, specifies the area for using Hypericum preparations (internally as drops or tablets) as being: "psychovegetative disturbances, depressive parathymic conditions, anxiety and/or nervous agitation". The antidepressant activity, which is comparable to that of the tricyclic antidepressants, of St. John's wort has been substantiated in a large number of placebo-controlled studies.

As a household remedy, St. John's wort oil is employed, in particular, for treating wounds and pain and in association with burns (L. Roth loc. cit.).

Due to the characteristic red colour and fluorescence of the oil, hypericin was initially assumed to be the active compound in the St. John's wort oil. The formula of hypericin is depicted below:

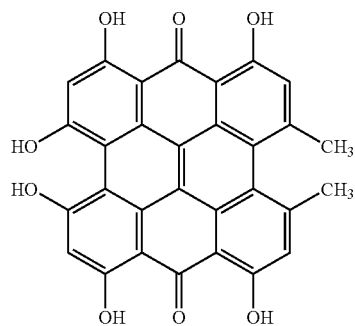

However, more recent investigations into the composition of St. John's wort oil have shown that it does not in fact contain any hypericin but instead what are termed oil hypericins, which are lipophilic products of the lysis of hypericin. In addition, St. John's wort oil contains hyperforin (P. Maisenbacher et al., Planta Med. 58:351–354 (1992) and B. Hellwig, DAZ 137, 29, pages 35–36), whose formula is depicted below:

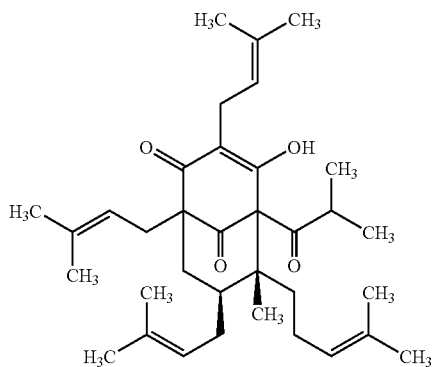

As an active compound, hyperforin has aroused interest as an antidepressant substance (Pharmacopsychiatry 1988, Vol. 31, Supplement 1, pages 1–60). In addition to this, hyperforin possesses antibacterial activity (A. I. Gurevich et al., L. Antibiotiki, 16:510–513 (1971).

Stable extracts prepared from Hypericum perforatum L. have been disclosed in DE 197 14 450 and DE 196 46 977.

DE 195 47 317 discloses an antiviral medicament which is based on St. John's wort active compounds and which comprises 1–50% hypericin or pseudohypericin.

EP-A-0 599 307 discloses a dry extract prepared from St. John's wort having an elevated content of hyperforin and also its use for producing drugs having psychovegetative and antidepressant activity.

Apart from St. John's wort oil, ointments are known which comprise a low concentration of Hypericum in addition to a variety of other medicinal herbs. Examples of these ointments are: "Unguentum Truw" for wound treatment and the homeopathic agent "Traumeel S", which is an antiinflammatory agent, and "Atemaron N R30", which is an analgesic/antirheumatic agent. It is not known whether these ointments contain hyperforin. However, because of the instability of hyperforin, it must be assumed that hyperforin is either not present, or only present in low quantities, if the extract is not prepared, stored and processed while being protected from light and oxidation. For example, it is not possible to detect any hyperforin in a commercially available Hypericum extract (Hyperforate).

In connection with topical use, and particularly in connection with treating inflammatory skin diseases, the known St. John's wort oil suffers from the disadvantage that, because of its fat content, it can only be used to a limited extent and is not suitable, for example, for treating eczemas. In addition to this, the oil only contains fat-soluble constituents of the St. John's wort and does not contain hypericin, for example.

Cytostatic agents inhibit the growth, in particular, of rapidly growing cells as are found in tumours and leukaemias. They are therefore suitable for use as chemotherapeutic agents for the treatment of cancer. While a large number of chemotherapeutic agents are known, these compounds also suffer from disadvantages. In particular, treatment with known chemotherapeutic agents is accompanied by pronounced side-effects and most chemotherapeutic agents only exhibit satisfactory activity towards particular tumour cell lines.

There therefore continues to be a need for additional compounds which are suitable for treating cancer.

An object of the present invention is therefore to make available an additional chemotherapeutic agent for treating cancer diseases.

Another object of the present invention is to make available a pharmaceutical formulation for the chemotherapeutic agent, which formulation does not suffer from the abovementioned disadvantages. In particular, it should be possible for the formulation to be adapted to a variety of skin conditions.

It has now been found, surprisingly, that hyperforin exerts a proliferation-inhibiting effect on tumour cells and can induce apoptosis in tumour cells.

The present invention consequently relates to the use of hyperforin for producing a drug for treating cancer diseases (primary tumors and metastases) and/or precancerous stages (cancer precursor stages).

In the present instance, cancer diseases are understood, in particular, as meaning malignant tumours and also lymphomas and leukaemias.

However, hyperforin is also particularly active against metastases, such as malignant melanoma (black skin cancer) metastases.

Hyperforin has also proved to be effective against epithelial tumours such as epithelial skin cancer. This cancer is a slowly growing skin cancer which is readily accessible to topical treatment. Epithelial skin cancer is also termed spinalioma, squamous cell carcinoma or prickle cell cancer. In addition to this, hyperforin is also suitable for treating precancerous stages such as solar precancerous stages.

In addition, hyperforin is suitable for treating mammary carcinomas (breast cancer).

In practice, it is of particular interest to use hyperforin in connection with lymphomas/leukaemias and difficulty operable tumours and for the adjuvant treatment of metastases. In particular, only very moderate success has been achieved with the therapies which are so far available for treating malignant melanoma.

Hyperforin can be administered intravenously for treating systemic tumours and metastases. For intravenous administration, the lyophilized or dried active compound can, for example, be dissolved freshly in physiological saline solution and immediately injected or infused. However, the active compound can also be administered orally, for example in tablet form.

However, hyperforin is also suitable for local administration, for example by means of injection or instillation (for example endoscopically as well) within or around the tumour. The active compound can, for example, be prepared for this purpose as described above for the intravenous administration. However, the active compound can also advantageously be applied by epicutaneous application, for example in the form of a cream, with this application form being particularly suitable, for example, for treating solar precancerous stages.

For local, epicutaneous application, the active compound can, for example, be dissolved in ethanol and worked into a greasy ointment base. This can take effect occlusively (under film) on the tumour, for example for a period of 24 hours. Particularly preferred ointments and creams are described in more detail below.

When the active compound is being worked up, attention must be paid to the fact that it is a light-sensitive substance which readily decomposes. Appropriate protection from light must therefore be ensured when the active compound is being isolated, stored and administered.

In the treatment, according to the invention, of cancer diseases and/or precancerous stages with hyperforin, the concentration of hyperforin at the site of action should be sufficiently high to ensure that an antiproliferative or apoptosis-inducing effect is elicited. The concentration which is required for this purpose can vary depending on the nature of the treated tumour and can be readily determined by the skilled person. For example, a hyperforin concentration of 50 µg/ml in the administered solution is advantageous in the case of injection into a tumour while an active compound concentration of 100 µg/µl is advantageous in connection with epicutaneous application. In the case of systemic use, the active compound should be injected in quantities which are sufficient to ensure that plasma levels of at least 50 µg/ml are achieved. This corresponds to a hyperforin quantity of about 5 mg/kg of patient body weight.

As another aspect of this invention, it has been found that hyperforin can advantageously be administered in a pharmaceutical formulation which is in the form of a topical ointment or cream which comprises at least 15 µg of hyperforin/ml.

The ointment or cream should contain a concentration of active compound which is as high as possible, preferably in the range of 0.02–20 mg of hyperforin/ml, more preferably in the range of 1–20 mg/ml and particularly preferably about 10 mg/ml (1% hyperforin).

In addition to the active compound hyperforin, the ointment or cream according to the invention can additionally comprise hypericins as additional active compounds. In this connection, the total concentration of the hypericins in the ointments or cream should be at least 15 µg/ml, preferably 20–150 µg/ml. In the present instance, hypericins are understood as meaning hypericin and its pharmaceutically active derivatives. These include, in particular, pseudohypericin, which differs from hypericin in that a methyl group is replaced with hydroxymethyl.

The abovementioned active compounds can be introduced into the ointment or cream either as pure substances or in the form of a St. John's wort extract of defined concentration. In this connection, the ointment or cream according to the invention preferably does not comprise any other plant extracts apart from the St. John's wort extract.

For example, a St. John's wort extract which contains at least 200 µg of hyperforin/ml and at least 200 µg of hypericins/ml is suitable for preparing the ointments or cream according to the invention. The extract employed preferably contains 200–100,000 µg/ml, in particular about 1000 µg of hyperforin/ml, and 200–1000 µg of hypericins/ml. With these active compound concentrations in the extract, the ointment or cream according to the invention should contain at least 5% by weight of the extract. Advantageously, an ointment according to the invention can, for example, contain about 15% by weight of the extract, and a cream according to the invention can contain about 10% by weight of the extract.

The total extract which is standardized for hyperforin and hypericin should be an ethanolic extract or an extract to which ethanol has been added. In this connection, the extracts can, for example, be commercially available total extracts (tinctures). The ethanol content is preferably between 20 and 60% v/v, preferably 40–50% v/v. These requirements are met, for example, by a total extract supplied by the company Caelo, which total extract is preferably employed in accordance with the invention and contains 240 µg of hyperforin/ml and 300 µg of hypericin/ml.

In principle, aqueous extracts, $CO_2$ extracts or fresh plant extracts are also suitable provided they meet the requirements for the content of active compound.

The St. John's wort extract which is used for the ointment or cream according to the invention is qualitatively and quantitatively analysed by means of high pressure liquid chromatography (HPLC) (P. Maisenbacher et al., Planta Med. 58:351–354 (1992)). The photometric method described in the "Deutsche Arzneimittel-Codex (DAC) [German Drug Codex]" is used for measuring the total hypericins.

Besides the active compound or the active compounds, the ointment or cream according to the invention can comprise various pharmaceutically tolerated cream or ointment bases. Examples of these are white vaseline, viscous paraffin, wool wax, ascorbyl palmitate, glycerol monostearate 60, tocopherol (vitamin E), cetyl alcohol, medium-chain triglycerides, yellow wax, propylene glycol, Macrogol-1000-glycerol monostearate, citric acid, ascorbic acid and other preservatives and distilled water.

A preferred ointment according to the invention comprises about 15% by weight of St. John's wort extract and white vaseline, viscous paraffin, wool wax and ascorbyl palmitate, in each case in suitable quantity.

A preferred cream according to the invention comprises about 10% by weight of St. John's wort extract and also white vaseline, glycerol monostearate 60, cetyl alcohol, medium-chain triglycerides, yellow wax, propylene glycol, Marcogol-1000-glycerol monostearate, citric acid and water, in each case in suitable quantity.

The present invention also relates to a process for preparing a topical ointment or cream, in which process hyperforin and, where appropriate, hypericins, or a St. John's wort extract which contains at least 200 µg of hyperforin/ml and at least 200 µg of hypericins/ml, is/are mixed with customary pharmaceutically tolerated adjuvants such that an ointment or cream having a minimum content of 15 µg of hyperforin/ml and, where appropriate, a minimum content of 15 µg of hypericins/ml, is obtained.

When a St. John's wort extract is used for preparing the ointment or cream according to the invention, this extract has, in order to protect the hyperforin from oxidation, to be stored in the dark and firmly sealed, and under a protective gas (e.g. argon), until it is processed.

The ointment or cream according to the invention is suitable, for example, for treating cancer diseases, precancerous stages, inflammatory skin diseases, geriatric skin and bacterial skin infections. Because of its fatty base, the ointment is particularly indicated in the case of dry, desquamative skin changes which are accompanied by pruritus or inflammations. The active compound content which is preferred for the ointment (i.e. 15% by weight) is somewhat higher than the active compound content which is preferred for the cream (i.e. 10% by weight), which latter is, because of its amphiphillic nature, particularly suitable for treating acute to subacute eczematous skin changes.

The ointment according to the invention is consequently particularly suitable for treating chronic and also superinfected eczemas, exsiccation eczemas, hyperkeratotic hand and foot eczemas, subacute to chronic atopic dermatitis (neurodermatitis), lichen simplex, contact eczemas, prurigo simplex subacuta and other prurigo types, and psoriaris vulgaris of the plaque type, and also geriatric skin.

The cream is particularly suitable for treating acute to subacute atopic dermatitis (neurodermatitis), acute to subacute contact eczemas, psoriasis and geriatric skin, and also for the after-treatment and relapse prophylaxis of all eczemas.

The ointment and the cream can also be used in veterinary medicine, for example for treating inflammatory and infected skin diseases, such as mastitis (udder inflammation).

From a concentration of 100 ng/ml and upwards, hyperforin has a proliferation-inhibiting effect on human keratinocytes and lymphocytes. In addition to this, it has been possible to demonstrate that hypericin has a proliferation-inhibiting effect on keratinocytes (HaCaT) and T cells and can induce apoptasis in these cells. This effect is partially mediated by the formation of free oxygen radicals.

Because of the possible photosensitization due to the optional content of hypericin in the ointment or cream according to the invention, investigations were carried out in order to determine whether local use of the hypericin-containing preparation according to the invention can lead to sunburn-like phenomena. These investigations did not show any risk of sunburn.

The ointment or cream according to the invention has the advantage that its base can be adapted to various skin conditions. Thus, the cream is particularly suitable for treating acute and subacute dermatoses while the ointment is suitable for treating chronic dermatoses. In addition to this, both fat-soluble (hyperforin) and water-soluble (hypericin) active compounds from St. John's wort can be worked into an ointment or cream base. This makes it possible to achieve an effect which is superior to that of the known St. John's wort oil. In addition, the penetration of active compounds from cream and ointment bases is superior to that of active compounds from oils.

The novel ointment or cream for local topical use decisively enriches the spectrum of therapies for inflammatory skin diseases such as neurodermatitis. In particular, the possibility exists of reducing cortisone therapy.

The attached FIG. 1 shows the antiproliferative effect of hyperforin on the tumour cell lines HT144 (human melanoma metastasis), A431 (human squamous cell carcinoma), Jurkat (human leukaemic lymphoma), 1F6 (human melanoma, primary tumour) and MT450 (rat mammary carcinoma) (Example 1).

The following examples are intended to clarify the invention. Commercially obtainable hyperforin from HWI Analytik, Rheinzabern, Germany, was used for Examples 1–6. The purity of the hyperforin was greater than 90%. In all the experiments, the solvent DMSO was tested at the maximum concentration used and did not show any effect on proliferation or apoptosis rate.

EXAMPLE 1

The antiproliferative effect of hyperforin on human and rat tumour cells was investigated in vitro. For this, tumour cells of the tumour cell lines HT144 (human melanoma metastasis), A431 (human squamous cell carcinoma), Jurkat (human leukaemic lymphoma), 1F6 (human melanoma, primary tumour) and MT450 (rat mammary carcinoma) were cultured, at a concentration of $1\times10^5$ cells/ml, in 1640 RPMI containing 10% foetal calf serum (FCS) containing 1% penicillin/streptomycin (all from Gibco) in 96-well microtitre plates (37° C., 5% $CO_2$). Hyperforin (HWI-Analytik) which had been freshly dissolved in DMSO was added, at various concentrations, to these cells for 24 h. 1 µCurie of $^3$H-thymidine (Amersham) was then added per well, and the incorporated radioactivity was measured in a scintillation counter (Canberra Packard) after 18 h. The radioactivity which is measured is proportional to the replication of the DNA in the cells.

Figure 1:
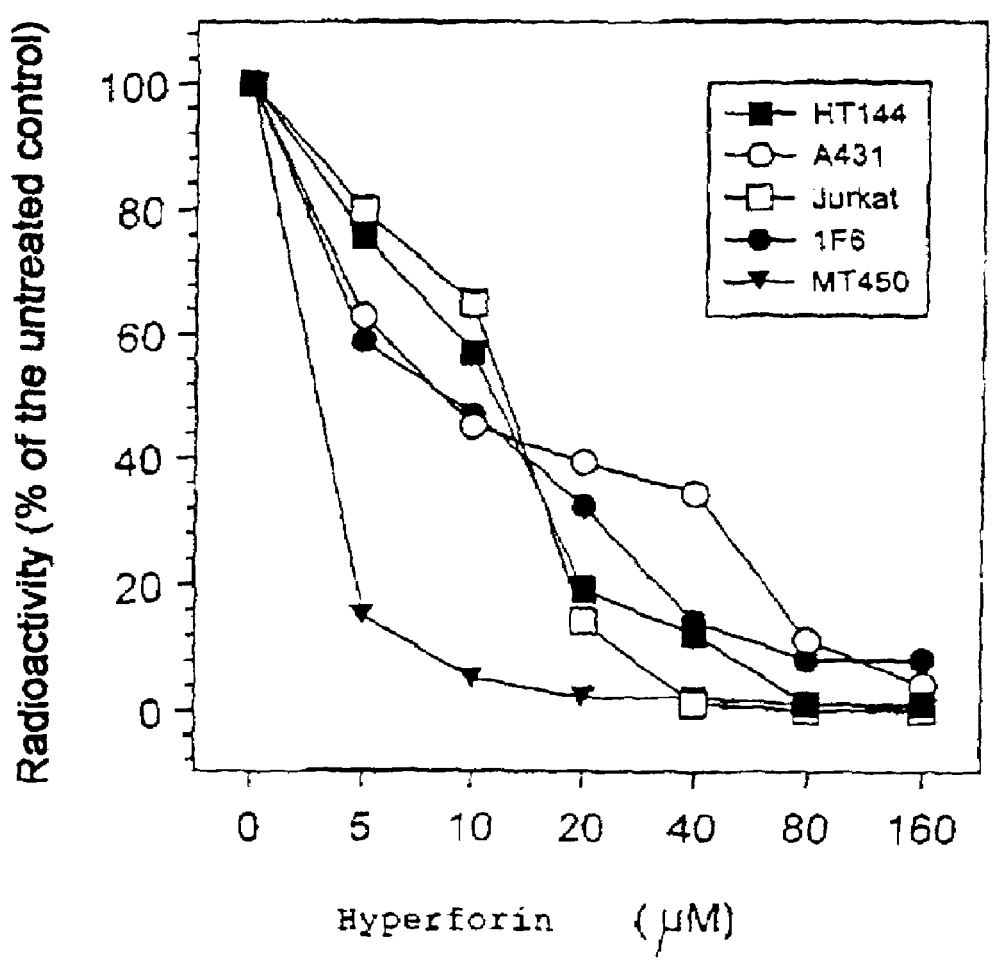

It can be seen from FIG. 1 that the concentration of hyperforin at which the growth of the cells was inhibited by 50% ($IC_{SC}$) was between 5 and 15 µm.

EXAMPLE 2

This example proves that hyperforin induces apoptosis, i.e. what is termed programmed cell death, in tumour cells. The induction of apoptosis in tumour cells is a characteristics feature of many cytostatic agents and provides supports for the view that hyperforin acts as such an agent.

HT144 (human melanoma metastasis), A431 (human squamous cell carcinoma), Jurkat (human leukaemic lymphoma), 1F6 (human melanoma, primary tumour) and MT450 (rat mammary carcinoma) tumour cells were cultured, at a concentration of $1\times10^4$ cells/ml, in 96-well microtitre plates. After the cells had been preincubated for 24 h, hyperforin was pipetted in to give the final concentrations shown in FIG. 2. The cells were then lysed and then examined for low molecular weight DNA fragments using a Cell Death Detection ELISA$^{PLUS}$ (Boehringer, Mannheim). For this, use was made of a biotinylated anti-histon antibody and a peroxidase-coupled anti-DNA antibody, and the proportion of low molecular weight DNA was determined by measuring the absorption of peroxidase at 405 nm.

Figure 2:
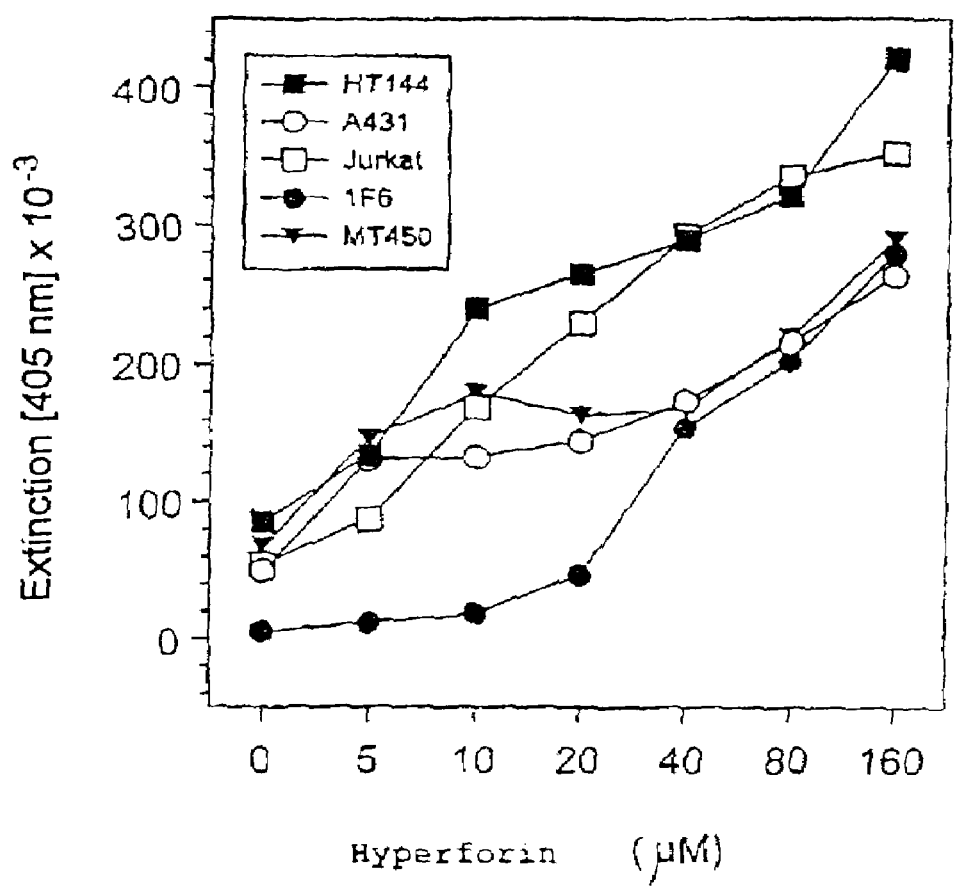
FIG. 2 shows the ability of hyperforin to induce apoptosis in the tumour cell lines HT144 (human melanoma metastasis), A431 (human squamous cell carcinoma), Jurkat (human leukaemic lymphoma), 1F6 (human melanoma, primary tumour) and MT450 (rat mammary carcinoma) (Example 2).

The results are shown in FIG. 2, which depicts the extinction at 405 nm after subtracting the untreated control. It can be seen that hyperforin induces apoptosis, in a dose-dependent manner, in all the tumour cell lines.

EXAMPLE 3

The toxic effect of various concentrations of hyperforin on the tumour cell lines HT144, A431 and Jurkat used in Examples 1 and 2 was investigated using a cytotoxicity assay. For this, membrane integrity was determined by means of trypan blue exclusion. The result is shown in Table 1, with the values being given in % of the untreated cells. It was scarcely possible to demonstrate any toxic effects, thereby confirming that hyperforin induces apoptosis specifically.

TABLE 1

| Hyperforin | Trypan blue exclusion (% of the cells) | | |
|---|---|---|---|
| (µg/ml) | HT144 | A431 | Jurkat |
| 0 | 100 | 100 | 100 |
| 2.5 | 100 | 100 | 100 |
| 5 | 100 | 100 | 100 |
| 10 | 100 | 100 | 100 |
| 20 | 100 | 95 | 100 |
| 40 | 90 | 90 | 100 |
| 80 | 80 | 90 | 100 |

EXAMPLE 4

The following example proves that hyperforin and the known cytostatic agent taxol, used as a comparison substance, induce apoptotic DNA fragmentation. The DNA fragmentation was determined by means of DNA gel electrophoresis. Jurkat (leukaemia) was used as the tumour cell line.

In each case $1\times10^6$ cells were incubated at 37° C. while being untreated or treated with hyperforin (40 µM) or taxol (10 µM), respectively. Apoptotic DNA fragments were isolated by means of lysis with NP 40. The cells were washed and pelleted after 4 hours or after 24 hours, respectively. The cell pellet was incubated for 10 sec. with lysis buffer (1% NP 40, Sigma; 20 mM EDTA, Sigma; 50 mM Tris-HCl, Sigma). the lysates were mixed with 1% SDS (Sigma), incubated at 56° C. for 2 h with RNase (5 µg/µl) (Boehringer), and digested with proteinase K (Sigma) (2.5 µg/µl) for 2 h at 37° C. After 10 M ammonium acetate had been added, the DNA was precipitated with 100% ethanol at −20° C. and analysed by means of gel electrophoresis on 1% agarose gels.

The results are shown in Table 2. It was found that hyperforin induces apoptosis in tumour cells more rapidly than does taxol, since the apoptosis was fully developed after only 4 hours.

TABLE 2

| | Untreated cells | Hyperforin (40 µM) | Taxol (10 µM) |
|---|---|---|---|
| 4 hours | − | ++ | + |
| 24 hours | − | ++ | ++ |

++ = strongly positive
+ = positive
− = negative

EXAMPLE 5

In order to demonstrate a possible mechanism of action for the induction of apoptosis by hyperforin, the activities of different caspases in tumour cell lines were investigated. The activation of caspases can be effected by a variety of signal transduction mechanisms and leads, by way of the activation of effector caspases (e.g. caspase 3) to induction of the programmed cell death. The activities of upstream caspase 9, downstream caspase 8 and effector caspase 3 were measured using a commercially available caspase kit (R&D Systems). MT450 cells were incubated with or without hyperforin (final concentration 50 µM) for 24 h at a concentration of 1 million cells/ml. After that, the cells were centrifuged down and the supernatant was removed; the cells were then lysed with lysis buffer. The cell lysate was in each case incubated with a substrate which was specific for the caspase and the cleavage product, which was coupled to a dye, was detected photometrically in an ELISA reader.

Figure 3:
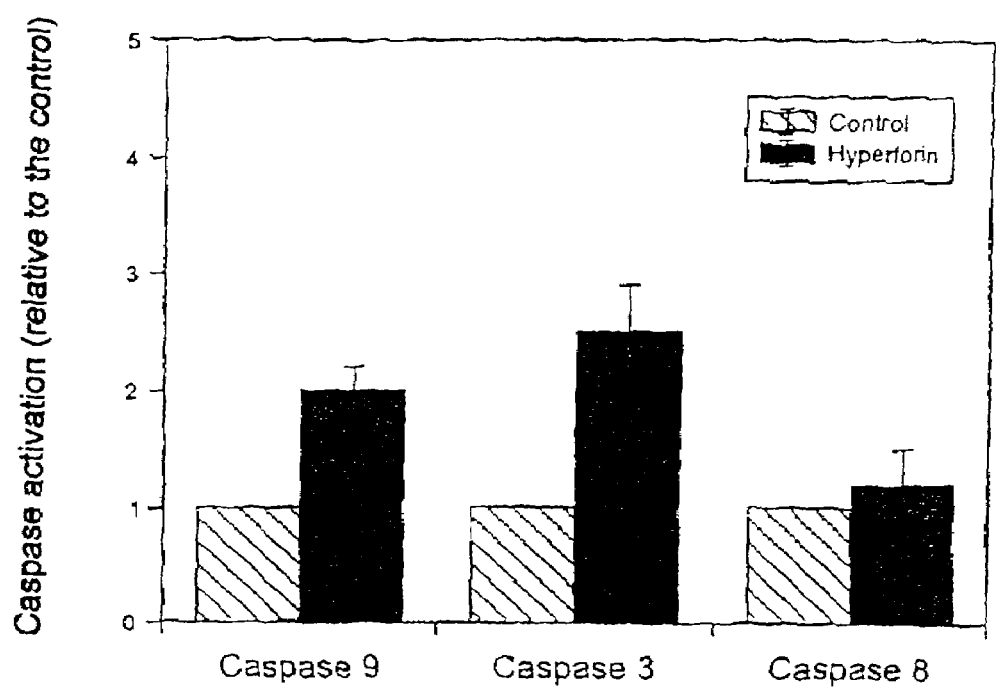
FIG. 3 shows the apoptosis, due to the selective activation of caspases 9 and 3, which is induced by hyperforin (Example 5).

The effect on caspase activity relative to the untreated control (control=1) is shown in FIG. 3. It is found that while hyperforin leads to an upregulation of caspase 9 and caspase 3, it does not lead to any activation of caspase 8.

EXAMPLE 6

Figure 4:
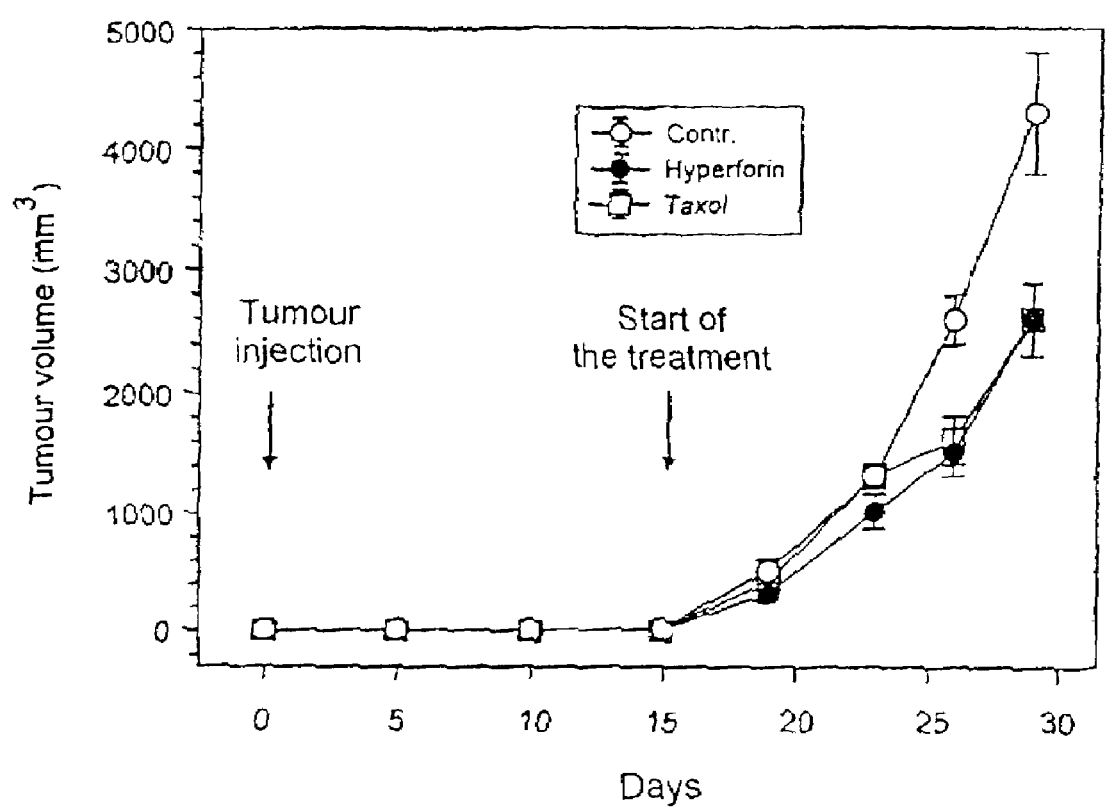
FIG. 4 shows the ability of hyperforin to inhibit the tumour growth of mammary carcinoma cells in vivo in a similar manner to taxol (Example 6).

The effect of hyperforin on the growth of MT450 cells (mammary carcinoma) was investigated in vivo in rats. A treatment with the same concentrations of the cytostatic agent taxol was carried out for comparison. Each treatment group consisted of 8 experimental animals; the treatment was carried out blind (blind experiment). 1 million tumour cells were injected into each animal. Intratumour injections were started after 3 weeks. The injections were performed daily, using in each case 100 µl of the solvent (10% in PBS), of the hyperforin (500 µg in 10% DMSO/PBS) or of the taxol (500 µg in 10% DMSO/PBS). The tumour volume was measured planimetrically 8 times, from the start of the tumour injections (day 0) until the conclusion of the treatment (day 30) and recorded as a growth curve (mean value +/− standard deviation) in FIG. 4. It is found that hyperforin significantly inhibits the growth of MT405 cells in vivo to the same extent as does taxol.

EXAMPLE 7

A St. John's wort ointment was prepared in accordance with the following recipe (values in % by weight):

| | |
|---|---|
| White Vaseline | 50.0 |
| Viscous paraffin | 9.0 |
| Wool wax | 25.0 |
| Ascorbyl palmitate | 1.0 |
| St. John's wort extract | 15.0 |
| | 100 |

The Vaseline, the viscous paraffin and the wool wax were heated to 60° C. in a water bath and mixed. The mixture was allowed to cool, while being stirred, with the ascorbyl palmitate being worked in during this period; the St. John's wort extract (total extract supplied by Caelo (hyperforin 240 µg/ml, hypericin 300 µg/ml)) was then worked in after the mixture had cooled down. The ointment which thus resulted contained 36 µg of hyperforin/ml and 45 µg of hypericin/ml.

EXAMPLE 8

A St. John's wort cream was prepared in accordance with the following recipe (values in % by weight):

| | |
|---|---|
| White Vaseline | 20.0 |
| Glycerol monostearate 60 | 4.0 |
| Cetyl alcohol | 6.0 |
| Medium-chain triglycerides | 8.0 |
| Yellow wax | 4.0 |
| Propylene glycol | 10.0 |
| Macrogol-1000-glycerol monostearate | 7.0 |
| Citric acid | 1.0 |
| Distilled water | 30.0 |
| St. John's wort extract | 10.0 |
| | 100 |

The vaseline, the glycerol monostearate 60, the cetyl alcohol, the medium-chain triglycerides and the yellow was were heated to 60° C. in a water bath and mixed. The Macrogol-1000-glycerol monostearate, the propylene glycol, the water and the citric acid were heated separately to 60° C. in a water bath and then worked into the first mixture. The resulting mixture was stirred until it had cooled down and the St. John's wort extract (total extract supplied by Caelo (hyperforin 240 µg/ml, hypericin 300 µg/ml)) was then worked in. The cream which thus resulted contained 24 µg of hyperforin/ml and 30 µg of hypericin/ml.

EXAMPLE 9

An extract supplied by Flavix (Rehlingen), which had a hyperforin content of 20% by weight (20 g/100 g) and to which neutral oil had been added, was used to prepare a hyperforin ointment or cream which contained a higher concentration of active compound. For this, 5 g of the extract were dissolved in 10 ml of 70% ethanol in order to obtain a starting solution having a hyperforin concentration of 100 mg/ml. This starting solution was worked into an ointment or cream base, in the manner described in Example 7 and Example 8, respectively, in place of the St. John's wort extract supplied by Caelo. Ointments and creams were prepared using the following recipes (values in % by weight):

| | 1% hyperforin | 0.1% hyperforin |
|---|---|---|
| a) Ointment | | |
| White Vaseline | 50.0 | 50.0 |
| Viscous paraffin | 9.0 | 9.0 |
| Wool wax | 30.0 | 39.0 |
| Ascorbyl palmitate | 1.0 | 1.0 |
| Starting solution | 10.0 | 1.0 |
| | 100.0 | 100.0 |
| b) Cream | | |
| White Vaseline | 20.0 | 20.0 |
| Glycerol monostearate | 4.0 | 4.0 |
| Cetyl alcohol | 6.0 | 6.0 |
| Medium-chain triglycerides | 8.0 | 17.0 |
| Yellow wax | 4.0 | 4.0 |
| Propylene glycol | 10.0 | 10.0 |
| Macrogol-1000-glycerol monostearate | 7.0 | 7.0 |
| Citric acid | 1.0 | 1.0 |
| Distilled water | 30.0 | 30.0 |
| Starting solution | 10.0 | 1.0 |
| | 100.0 | 100.0 |

EXAMPLE 10

The immunomodulatory effects of the novel preparation on the skin were examined in humans (3×4 test subjects) ex vivo after using the St. John's wort ointment from Example 7 in comparison with St. John's wort oil. For this, skin samples, which had been subjected to different treatments, were removed from voluntary test subjects and an investigation was carried out in order to determine whether the ability of epidermal Langerhans cells to present antigen is being affected.

In detail, the following MECLR (mixed epidermal cell leukocyte reaction) was carried out: In 4 test subjects in each case, circular test areas of 2 cm in diameter on the flexor sides of the forearm were treated either with St. John's wort oil, St. John's wort cream or the treatment base, and the effect was examined in comparison with untreated skin. 100 µl of the test substances were applied for 24 h in epicutaneous test chambers. After that, the residues were removed and epidermal suction blisters were produced using a vacuum. The roof of the blister was dissected out under sterile conditions using a scalpel and a suspension of epidermal cells (EC) was prepared by treating with trypsin. 50,000 EC were cocultured for 6 days (37° C., 5% $CO_2$) with 150,000 T cells (TC) in RPMI 1640 containing 10% foetal calf serum (FCS) containing 1% penicillin/streptomycin (all from Gibco) in 96-well flat-bottomed microtitre plates (Greiner). 1 µCurie of $^3$H-thymidine (Amersham) was then added per well and the radioactivity which was incorporated was measured in a scintillation counter (Canberra Packard). The radioactivity which is measured is proportional to the replication of the DNA in the cells.

Figure 5:
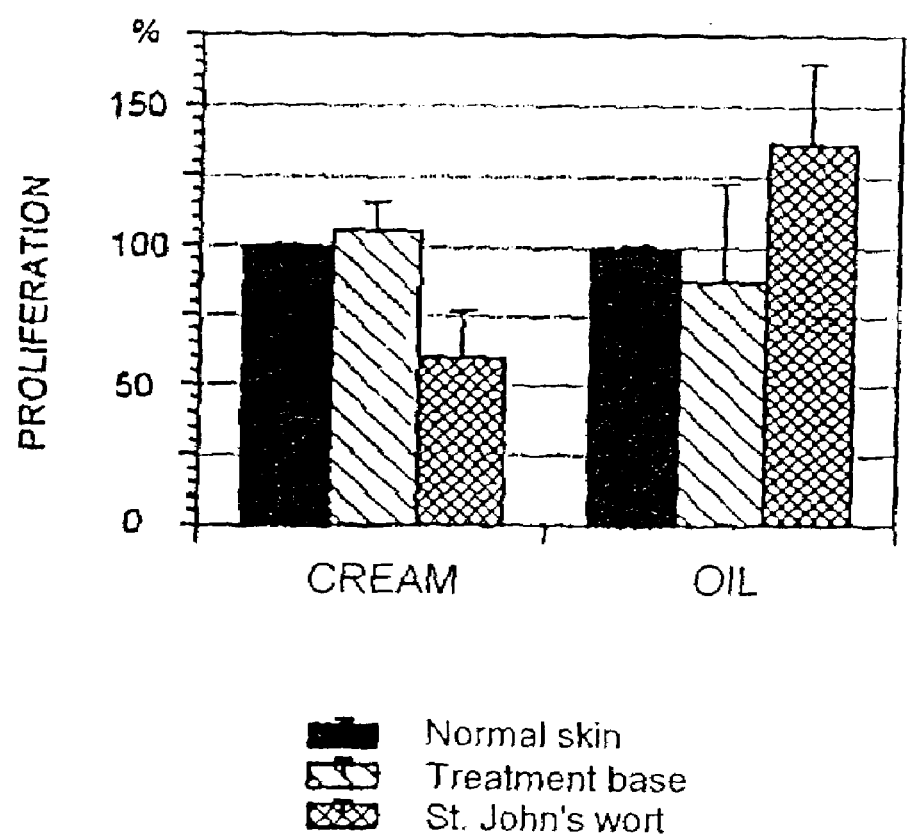
FIG. 5 shows the proliferation-inhibiting effect on the cream according to the invention, as compared with that of St. John's wort oil, following use on healthy test subjects in vivo (Example 9).

These investigations showed that the St. John's wort ointment according to the invention brings about an inhibition of proliferation. On the other hand, the use of St. John's wort oil results in an increase in proliferation (FIG. 5).

These results provide support for the St. John's wort ointment according to the invention having an antiinflammatory effect which was not detectable in the case of the oil.

EXAMPLE 11

In a unilateral experiment carried out on a patient suffering from eczema, one lower leg was treated for two weeks with St. John's wort oil while the other was treated with the novel St. John's wort ointment as described in Example 7. At the time of inspection, the lower leg which had been treated with the ointment had recovered very well while the lower leg which had been treated with the oil had, if anything, deteriorated.

EXAMPLE 12

Four patients suffering from different forms of localized eczema were treated. After the experiment had been explained and the patients had consented, the eczemas were documented photographically and the patients carried out a monotherapy with the ointment according to the invention over a period of 2 weeks. After that, the eczema were documented photographically once again. Complete healing was achieved in two of the patients while the condition was substantially improved in the other patients. The results of this treatment are summarized in Table 3.

TABLE 3

| No. | Sex | Diagnosis | Treatment | Success of the therapy |
|---|---|---|---|---|
| 1 | female | Eczema in the hollow of the elbow or knee | Hypericum cream | healed |
| 2 | male | Eczema of the hand | Hypericum cream | improved |
| 3 | female | Neurodermatitis of the arms | Hypericum cream | healed |
| 4 | female | Prurigo of the lower leg | Hypericum cream | improved |

EXAMPLE 13

Figure 6:
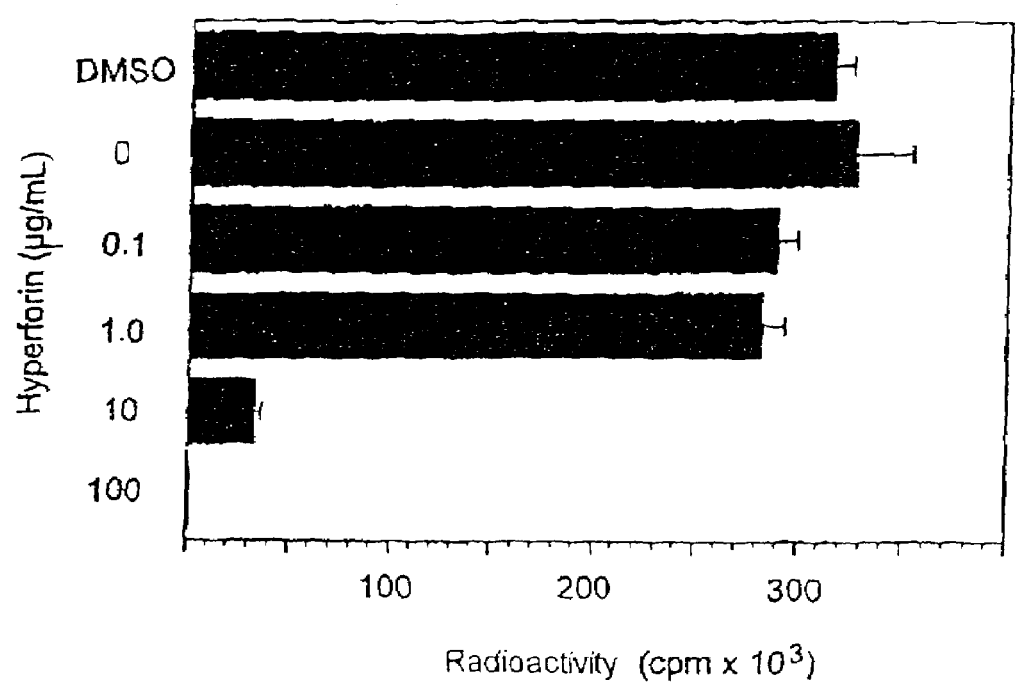
FIG. 6 shows the proliferation-inhibiting effect of hyperforin on HaCaT cells in vitro (Example 13).

This example demonstrates the proliferation-inhibiting effect of hyperforin on keratinocytes. HaCaT cells were cultured (37° C., 5% $CO_2$) in keratinocyte medium containing 10% foetal calf serum (FCS) containing 1% penicillin/streptomycin (all from Gibco). Subconfluent cultures were detached using EDTA-trypsin (Gibco), washed 3× in PBS and then cultured for a further 24 h (until adherence) at a density of 20,000/well in 96-well flat-bottomed microtitre plates (Greiner). After that, hyperforin (HWI-Analytik) which had been freshly dissolved in DMSO was added for a period of 24 h. 1 µCurie of $^3$H-thymidine (Amersham) was then added per well and the incorporated radioactivity was measured in a scintillation counter (Canberra Packard). The radioactivity which is measured is proportional to the replication of the DNA in the cells. The results for hyperforin concentrations of from 0 to 100 µg/ml are depicted in FIG. 6, where cpm denotes counts per minute. It is found that proliferation is virtually completely inhibited at a hyperforin concentration of 100 µg/ml.

EXAMPLE 14

Figure 7:
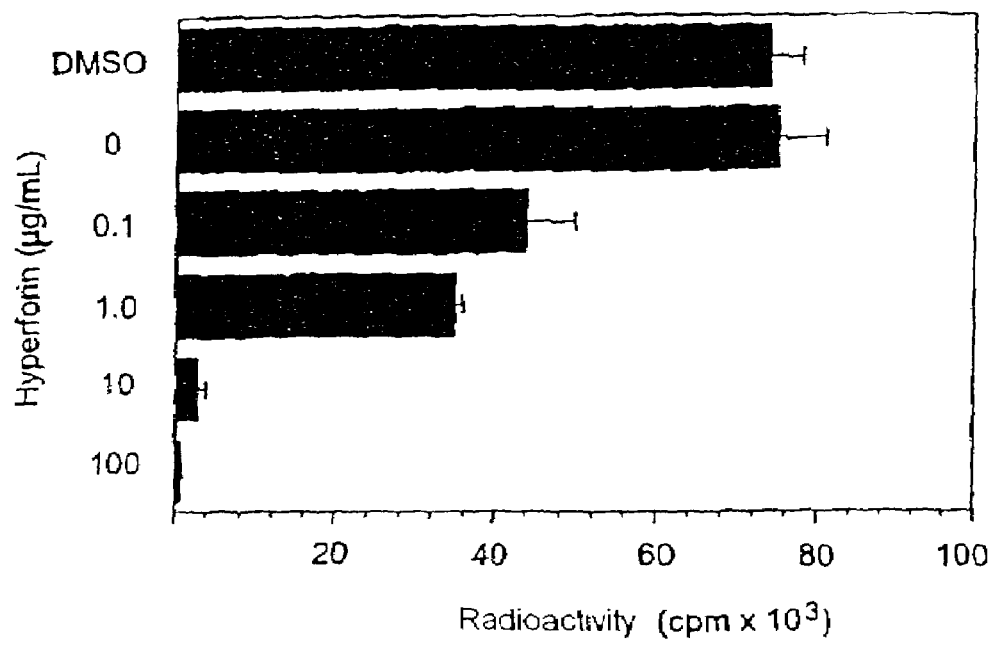
FIG. 7 shows the proliferation-inhibiting effect of hyperforin on PBMC in vitro (Example 14).

This example demonstrates the proliferation-inhibiting effect of hyperforin on peripheral blood mononuclear cells (PBMC). PBMC were isolated from heparinized blood by density gradient centrifugation using Ficoll (Seromed). The PBMC were washed 3× in PBS and cultured for 24 h (37° C., 5% $CO_2$) in RPMI 1640 containing 10% foetal calf serum (FCS) containing 1% penicillin/streptomycin (all from Gibco) in 96-well flat-bottomed microtitre plates (Greiner) at a density of 200,000/well. After that, the cells were stimulated with 1 µg/ml phytohaemagglutinin (PHA) (Wellcome), and hyperforin (HWI-Analytik) which had been freshly dissolved in DMSO was added for a period of 24 h. 1 µCurie of $^3$H-thymidine (Amersham) was then added per well and the incorporated radioactivity was measured in a scintillation counter (Canberra Packard). The radioactivity which is measured is proportional to the replication of the DNA in the cells. The results for hyperforin concentrations of from 0 to 100 µg/ml are depicted in FIG. 7, where cpm denotes counters per minute. It is found that even small concentrations of hyperforin have a proliferation-inhibiting effect on PBMC and proliferation is virtually completely inhibited at a concentration of 100 µg/ml.

EXAMPLE 15

This example shows that hyperforin cream containing a high proportion of hyperforin has an immunomodulatory effect in vivo. It was possible to demonstrate, by means of experiments using purified hyperforin, that this immunomodulatory effect is to be attributed to the hyperforin.

The immunomodulatory effect of the cream according to the invention was tested ex vivo in humans (in each case 4 test subjects). For this, skin samples which had been treated in different ways were removed and an investigation was carried out to determine whether the ability of epidermal Langerhans cells to present antigen is affected. In detail, this was investigated in an MECLR (mixed epidermal cell leukocyte reaction): In 4 test subjects in each case, round test areas of 2 cm in diameter on the flexor side of the lower arm were treated with Hypericum cream (containing 24 µg of hyperforin/ml and 30 µg of hyperin/ml), with hyperforin cream (24 µg/ml) or with sun simulator irradiation (144 $J/cm^2$). Untreated skin and the use of the vehicle without active compounds served as the controls. 100 μl of the test substances were applied for 24 h in epicutaneous test chambers. After that, the residues were removed and an epidermal suction blister was produced using a vacuum. The roof of the blister was dissected out under sterile conditions using a scalpel and a suspension of epidermal cells (EC) was prepared by treating with trypsin. 50,000 EC were cocultured for 6 days (37° C., 5% $CO_2$) with 150,000 TC (T cells) in 1640 RPMI containing 10% foetal calf serum (FCS) containing 1% penicillin-streptomycin in 96-well flat-bottoms microtitre plates (Greiner). 1 μCurie of $^3$H-thymidine (Amersham) was then adder per well and, after 18 h, the incorporated radioactivity was measured in a scintillation counter (Canberra Packard). The radioactivity which is measured is proportional to the replication of the DNA in the cells.

Figure 8:
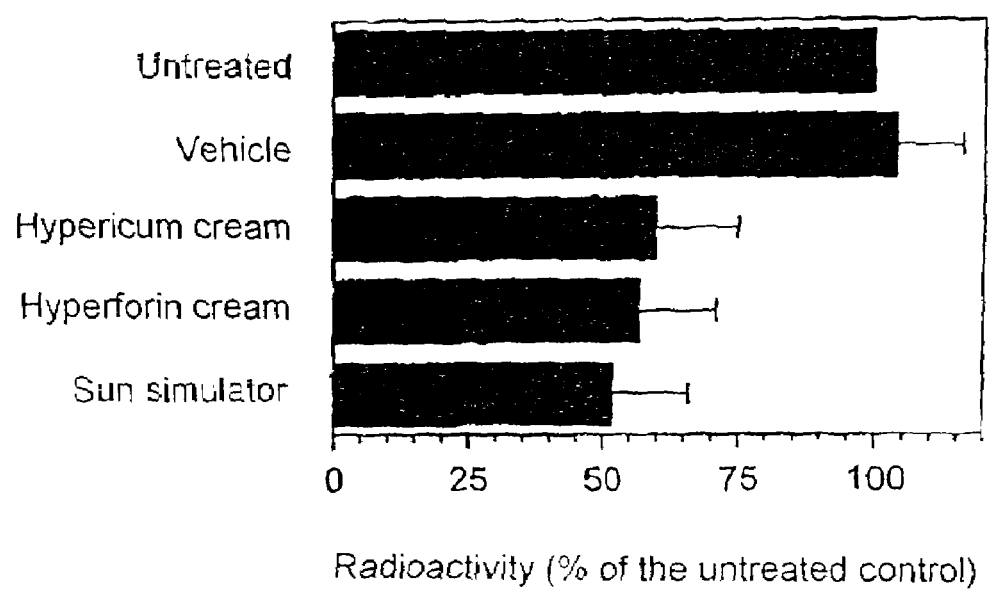
FIG. 8 shows the proliferation-inhibiting effect of a cream which was standardized for hyperforin and of a Hypericum cream as compared with the immunosuppressive effect of a sun simulator irradiation (two times MED). Untreated skin was tested as the control (Example 15).

The results (FIG. 8) show that the hyperforin-containing St. John's wort cream and the hyperforin cream significantly inhibit proliferation to the same order of magnitude as does irradiation with the sun simulator.

This example demonstrates the proliferation-inhibiting effect of hyperforin in vitro. In all cases, use was made of pure hyperforin from HWI-Analytik (Rheinzabern). The purity of the hyperforin was >90%. In all the in-vitro experiments, the solvent DMSO was tested at the maximum concentration employed and did not exhibit any effect on the proliferation and vitality of the cells. Normal skin samples were removed from healthy test subjects; these samples were then incubated with hyperforin in vitro and an investigation was carried out to determine whether the ability of epidermal Langerhans cells to present antigen is affected.

This was investigated in an MECLR (mixed epidermal cell leukocyte reaction) as described in Example 14: In 4 test subjects in each case, epidermal suction blisters were produced on the flexor side of the lower arm using a vacuum. The roof of the blister was dissected out under sterile conditions using a scalpel and a suspension of epidermal cells (EC) was prepared by treating with trypsin. A part of the EC or the TC was in each case incubated for 24 h with 24 μg of hyperforin/ml. After that, the cells were washed and 50,000 EC were cocultured for 6 days (37° C., 5% $CO_2$) with 150,000 TC (T cells) in 1640 RPMI containing 10% foetal calf serum (FCS) containing 1% penicillin-streptomycin in 96-well flat-bottomed microtitre plates (Greiner). 1 μCurie of $^3$H-thymidine (Amersham) was then added per well and, after 18 h, the incorporated radioactivity was measured in a scintillation counter (Canberra Packard). The radioactivity which is measured is proportional to the replication of the DNA in the cells.

Figure 9:
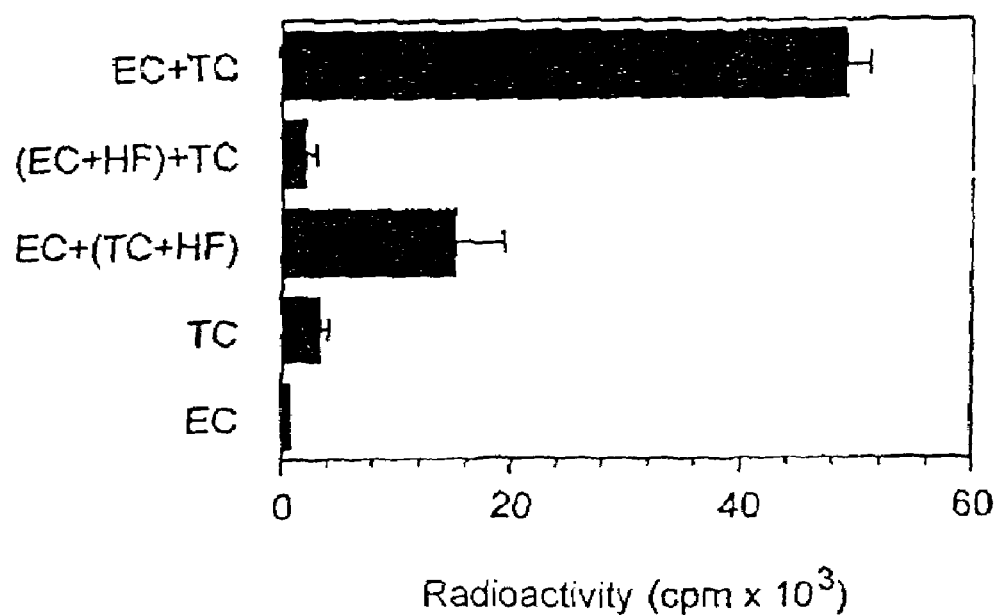
FIG. 9 shows the proliferation-inhibiting effect of hyperforin in vitro (Example 16).

The results (FIG. 9) show that hyperforin significantly inhibits proliferation both when acting on EC and when acting on TC.

The invention claimed is:

1. A method for treating a skin condition, comprising administering to a subject in need thereof an effective amount of a composition consisting of (a) pharmaceutically acceptable carrier and (b) active agent consisting of hyperforin and hypericin.

2. The method according to claim 1, wherein the skin condition is eczema.

3. The method according to claim 1, wherein said condition is selected from the group consisting of exsiccation eczema, hyperkeratotic hand and foot eczemas, contact eczemas, atopic dermatitis, neurodermatitis, lichen simplex, and prurigo simplex.

4. The method according to claim 1, wherein said subject is a mammal.

5. The method according to claim 1, wherein said composition is in the form of a topical ointment and said effective amount consists of at least 15 μg hyperforin per ml of the composition.

6. The method according to claim 1, wherein said composition is in the form of a topical ointment and said effective amount is 0.02–20 mg hyperforin per ml of the composition.

7. The method according to claim 6 wherein said effective amount is 1–20 mg hyperforin per ml of the composition.

8. The method according to claim 7 wherein said effective amount is 10 mg hyperforin per ml of the composition.

9. The method according to claim 1, wherein said effective amount is at least 15 μg hypericin per ml of the composition.

10. The method according to claim 1, wherein said effective amount of hyperforin is 20–150 μg hypericin per ml of the composition.

11. The method of claim 1, wherein said hyperforin is at least 90% pure.

12. A method for treating a tumor, comprising administering to a subject in need thereof an effective amount of a composition consisting of (a) pharmaceutically acceptable carrier and (b) active agent consisting of (i) hyperforin or (ii) hyperforin and hypericin.

13. The method according to claim 12, wherein said tumor is selected from the group consisting of a lymphoma, leukemia, melanoma, an epithelial tumor, and a metastatic tumor.

14. The method according to claim 12, wherein said subject is a mammal.

15. The method according to claim 12, wherein said composition is in the form of a topical ointment and said effective amount consists of at least 15 μg hyperforin per ml of the composition.

16. The method according to claim 12, wherein said composition is in the form of a topical ointment and said effective amount is 0.02–20 mg hyperforin per ml of the composition.

17. The method according to claim 16 wherein said effective amount is 1–20 mg hyperforin per ml of the composition.

18. The method according to claim 17 wherein said effective amount is 10 mg hyperforin per ml of the composition.

19. The method according to claim 12, wherein said effective amount is at least 15 μg hypericin per ml of the composition.

20. The method according to claim 12, wherein said effective amount of hypericin is 20–150 μg hypericin per ml of the composition.

21. The method of claim 12, wherein said hyperforin is at least 90% pure.

22. The method of claim 1, wherein said skin condition is selected from the group consisting of inflammatory skin condition, a precancerous skin condition, a geriatric skin condition, and a microbial skin infection.

* * * * *